(12) United States Patent
Johnson et al.

(10) Patent No.: US 6,761,730 B1
(45) Date of Patent: Jul. 13, 2004

(54) PORTABLE FEET TANNING DEVICE

(76) Inventors: William Johnson, 4040 42nd St., Sarasota, FL (US) 34235; Colleen Johnson, 4040 42nd St., Sarasota, FL (US) 34235

(*) Notice: Subject to any disclaimer, the term of this patent is extended or adjusted under 35 U.S.C. 154(b) by 183 days.

(21) Appl. No.: 10/177,413

(22) Filed: Jun. 21, 2002

(51) Int. Cl.[7] ................................. A61N 5/06
(52) U.S. Cl. ........................... 607/94; 607/90
(58) Field of Search ................ 607/88, 90, 94

(56) References Cited

U.S. PATENT DOCUMENTS

| | | | |
|---|---|---|---|
| 1,280,857 A | | 10/1918 | Ruiter |
| 1,337,798 A | | 4/1920 | Ruiter |
| 1,660,794 A | | 2/1928 | Hudson |
| 1,718,770 A | | 6/1929 | Zublin |
| 2,054,332 A | | 9/1936 | Lower et al. |
| 2,311,415 A | | 2/1943 | Rouat |
| 2,444,379 A | | 6/1948 | Sexton |
| 3,101,716 A | | 8/1963 | Cornell, Jr. |
| 4,287,554 A | | 9/1981 | Wolff |
| 4,984,571 A | * | 1/1991 | Springer et al. ............ 607/94 |
| 5,282,842 A | * | 2/1994 | Changaris ............ 607/88 |
| 5,466,248 A | | 11/1995 | Whitson-Newman |
| 5,837,000 A | * | 11/1998 | Boudreau ............ 607/95 |
| 6,139,568 A | * | 10/2000 | Doty ............ 607/91 |
| 6,273,906 B1 | | 8/2001 | Swanson |
| 6,309,366 B1 | | 10/2001 | Maxwell |
| 6,478,810 B1 | * | 11/2002 | Purschel ............ 607/91 |
| 6,494,901 B1 | * | 12/2002 | Doty ............ 607/91 |
| 6,676,687 B2 | * | 1/2004 | Stoppler ............ 607/94 |

* cited by examiner

Primary Examiner—Roy D Gibson
Assistant Examiner—Henry M. Johnson, III
(74) Attorney, Agent, or Firm—Michael I. Kroll

(57) ABSTRACT

The present invention 10 discloses a portable foot tanning device which provides an enclosure 30 for containing the feet 18 of a user 14. The present invention 10 has a concave inside reflective surface 28 which acts like lenses, focusing lights emitted by the tanning lamp 16 toward the center of the cavity 36. A transparent feet compartment liner 20 protects feet 18 from the heat of the tanning lamp 16 by preventing direct contact. A mechanical interlock 22 prevents the lamp(s) from being activated without the liner in place. An alternative embodiment of the present invention 10 is envisioned, in which the front portion of the tanning lamp 16 and control device assembly is hinged at 38 on top, thereby allowing it to be opened upward to a predetermined height that allows the lamp 16 to be pointed outward, thereby allowing tanning on other parts of the body of a user 14 positioned in the front and outside of the device.

16 Claims, 10 Drawing Sheets

PORTABLE FEET TANNING DEVICE

BACKGROUND OF THE INVENTION

1. Field of the Invention

The present invention relates generally to foot-care device, and, more specifically, to a portable foot tanning device. Although other foot-care, tanning devices have been devised, the current invention provides the convenience of compact, energy efficient, ergonomic and a multi-functional tanning device that the prior arts lack.

The current invention provides an additional element in the form of a hinged panel having the lamp assembly thereon that can be swung through approximately 270° and hingedly positioned to a point whereby the tanning device can be used on other body parts.

Feet tanning not only provides care for the feet in terms of circulation and hygiene, but it also provides cosmetic benefits in that the feet look healthier and blend in with the rest of a tanned leg by eliminating tan lines.

The current invention is, in its basic form, an enclosure. In the enclosure is found a lamp that can be energized to emit UVA and/or UVB rays within the interior. In its basic form, the device can be solid on the outside. The removable feet compartment allows access to the internals.

An aperture is positioned on the top of the device wherethrough one of more feet can be inserted for tanning purposes. The aperture is not sealed like other prior art device which in themselves would create tan lines having appendage gripping members. The natural, loose allowance in space around the ankle makes it possible for the degree of tanning to be graduated, thereby eliminating tan lines.

Upper front portion of the device, directly above the tanning lamp, is slotted for the passage of hot air from the inside. This hot air can be allowed to escape naturally, or forced by the cooling fan.

The rest of the front portion of the device, directly behind the tanning lamp, is used to equip control devices such as timer and switch as well as a handle and air-intake openings.

What makes the current invention energy efficient is the inside reflective surfaces that are also gently curved, which act like lenses, focusing lights emitted by the tanning lamp to the center of the void.

The center portion of the void is separated from the tanning lamp by the transparent feet compartment liner that protects feet from the heat of the tanning lamp by preventing direct contact. This liner is designed to contain the feet and can be removed for external cleaning and sterilization. A mechanical interlock prevents the lamp(s) from being activated without the liner in place.

The front portion of the device where the tanning lamp and the control devices are found is generally shaped convex, reminiscent of a half sphere. The alternative embodiment of the current invention is envisioned, in which the front portion of the tanning lamp and control device assembly is hinged on top, thereby allowing it to be opened upward to a predetermined height such that the assembly is fixable in between by means therefor. This allows the lamp to be pointed outward and toward the front of the device, thereby allowing tanning on other parts of the body of a user positioned in the front of the device.

2. Description of the Prior Art

There are other tanning devices designed for portable tanning. Typical of these is U.S. Pat. No. 1,280,857 issued to V. L. Ruiter on Oct. 8, 1918.

Another patent was issued to V. L. Ruiter on Apr. 20, 1920 as U.S. Pat. No. 1,337,798. Yet another U.S. Pat. No. 1,660,794 was issued to W. Hudson on Feb. 28, 1928 and still yet another was issued on Jun. 25, 1929 to M. N. Zublin as U.S. Pat. No. 1,718,770.

Another patent was issued to Lower, et al., on Sep. 15, 1936 as U.S. Pat. No. 2,054,332. Yet another U.S. Pat. No. 2,311,415 was issued to R. Rouat on Feb. 16, 1943. Another was issued to J. T. Sexton on Jun. 29, 1948 as U.S. Pat. No. 2,444,379 and still yet another was issued on Aug. 27, 1963 to E. S. Cornell, Jr. as U.S. Pat. No. 3,101,716.

Another patent was issued to F. Wolff on Sep. 1, 1981 as U.S. Pat. No. 4,287,554. Yet another U.S. Pat. No. 5,466,248 was issued to J. Whitson-Newman on Nov. 14, 1995. Another was issued to J. D. Swanson on Aug. 14, 2001 as U.S. Pat. No. 6,273,906 and still yet another was issued on Oct. 30, 2001 to R. E. Maxwell as U.S. Pat. No. 6,309,366.

U.S. Pat. No. 1,280,857

Inventor: V. L. Ruiter

Issued: Oct. 8, 1918

This invention has for its object a novel and efficient therapeutic apparatus in which various diseases and ailments of the limbs of the body may be effectively treated by the application of an intense dry heat and strong rays of light.

U.S. Pat. No. 1,337,798

Inventor: V. L. Ruiter

Issued: Apr. 20, 1920

One of the main objects of the invention is to provide an apparatus of the character stated by means of which the lower potion of the body may be subjected to the action of heat and light rays from all sides thereof so as to effectually penetrate the body so as to kill the disease germs and reduce inflammation and promote circulation.

U.S. Pat. No. 1,660,794

Inventor: W. Hudson

Issued: Feb. 28, 1928

In a therapeutic appliance for the purpose described, an inlet for alternating current, an inlet for direct current, a resistance element comprising a plurality of turns of resistance wire, and having one end connected to the direct current circuit and the other end connected to the alternating current circuit and a regular arm engaging said resistance and having a connection to both the direct current and alternating current line, whereby a portion of the resistance is included in the direct current circuit and another portion of said resistance in included in the alternating current circuit.

U.S. Pat. No. 1,718,770

Inventor: M. N. Zublin

Issued: Jun. 25, 1929

The invention provides a reducing and light treatment cabinet in which a person with a weak heart may be effectively treated. In actual practice, it is possible to keep a patient having a weak heart in a cabinet of the invention for twenty-eight minutes at a temperature of 120° F., whereas the patient can be kept only ten minutes in the common type of cabinet and only at a temperature of 80° F.

U.S. Pat. No. 2,054,332

Inventor: A. E. Lower, et al.

Issued: Sep. 15, 1936

The invention relates to therapeutic lamps and particularly to one of a type designed for treating the feet and the lower portions of the legs of a patient. The principal objects of the invention are to provide an electric apparatus of this character so constructed that a great concentration of heat or light rays on the members being treated may be had with a relatively low consumption of electric current; one in which such heat or rays may be selectively directed against the feet from different directions and with different intensities without moving the feet and without the use of any complicated electrical apparatus; and one in which a comfortable support for the feet is provided, which may be manipulated by the patient to alter the position of the feet in the zone of heat as may be desired and arranged so that the entire area of the feet is exposed to the heat and light rays.

U.S. Pat. No. Des. 2,311,415

Inventor: R. Rouat

Issued: Feb. 16, 1943

The invention relates to an electric bath and particularly to a bath in which the beneficial rays and heat from the electric element are reflected and projected onto and into the body of the bather while enclosed and reclining.

U.S. Pat. No. 2,444,379

Inventor: J. T. Sexton

Issued: Jun. 29, 1948

This invention relates to ray treating appliances of the portable character, and has for its primary aim to provide a therapeutic cabinet, designed to house ray lamps of the type known to be helpful in the treatment of skin diseases and that has unique structure for holding the member being treated in, proper position with respect to said lamps.

U.S. Pat. No. 3,101,716

Inventor: E. S. Cornell, Jr.

Issued: Aug. 27, 1963

This invention relates to apparatus for treating parts of the human body with radiation and in particular skin diseases of the feet and hands, for example, athlete's foot.

U.S. Pat. No. 4,287,554

Inventor: F. Wolff

Issued: Sep. 1, 1981

Apparatus for producing ultraviolet radiation, particularly a quick-tanning or therapeutic sunlamp, has a source of substantially uniform ultraviolet radiation, including at least two closely adjacent tubular low-pressure mercury lamps; an arrangement for intercepting at least the major percentage of wavelength bands of ultraviolet radiation below approximately 300 mm; and a reflector system cooperating with said source and defining at least one opening for the escape of ultraviolet radiation consisting essentially of the remaining wavelength band of ultraviolet radiation, said reflector system including for each of said lamps a trough-shaped reflector surrounding the lamp along an arc, and at least one intermediate portion between adjacent ones of said lamps and two lateral portions having zones which project forwardly of said intermediate portion and have forward edge portions defining said opening, the space between said lateral portions and forwardly of said intermediate portion being substantially unobstructed, and the source and reflector system cooperating to establish in the vicinity of the opening a high-density radiation field, the heat output of said lamps being sufficiently low so that the temperature in the region of said radiation field is below the range of discomfort of a person exposed to the field. The apparatus may include a mirror flanked by the lamps so that a user can enjoy the benefits of the ultraviolet radiation at no additional expenditure of time while looking into the mirror for other purposes.

U.S. Pat. No. 5,466,248

Inventor: J. C. Whitson-Newman

Issued: Nov. 14, 1995

A foot ghost ender comprised of a rounded steel shell having a front, a back, a left sidewall, a light sidewall, an open top, a closed bottom, an inner surface, and an outer surface. An aperture is formed in the right sidewall. An extension is integral with the open top. The extension has an open circular top. A plurality of tanning lamps are secured to the inner surface of the rounded steel shell. An adjustable foot rest is secured to the inner surface of the rounded steel shell. The device also contains a retractable power cord having a first end, and a second end. The first end is received through the aperture formed within the right sidewall of the rounded steel shell. A three-prong polarized plug secured to the first end. A control panel with adjustable timer is secured to the right sidewall of the rounded steel wall. The adjustable timer functions to turn the tanning lamps on and off.

U.S. Pat. No. 6,273,906

Inventor: J. D. Swanson

Issued: Aug. 14, 2001

A device for tanning the feet of athletes who develop tanned legs while wearing shorts to participate in outdoor activities. The tanning device also includes a fungicidal mechanism for killing foot funguses as well as a foot massaging mechanism for providing soothing vibrations to the feet while the user is receiving a tanning treatment.

U.S. Pat. No. 6,309,366

Inventor: R. E. Maxwell

Issued: Oct. 30, 2001

A foot therapy device including a portable housing with an annular wall having an upper edge and defining a reservoir for retaining a volume of liquid to be used during foot therapy; a lid covering a given portion of the reservoir and secured to a continuous portion of the upper edge; and a liquid seal member disposed between the lid and the given upper edge portion.

While these foot care and tanning devices may be suitable for the purposes for which they were designed, they would not be as suitable for the purposes of the present invention, as hereinafter described.

SUMMARY OF THE PRESENT INVENTION

The present invention discloses a portable foot tanning device for containing the feet of a user which may be alternatively equipped to provide an enclosure having an additional element in the form of a hinged panel having the lamp assembly thereon that can be swung through approximately 270 degrees and hingedly positioned to a point whereby the tanning device can be used on other body parts of a user outside the enclosure. The present invention is energy efficient due to the inside reflective surfaces that are also gently curved, which act like lenses, focusing lights emitted by the tanning lamp to the center of the cavity. The center portion of the cavity is separated from the tanning lamp by the transparent feet compartment liner that protects feet from the heat of the tanning lamp by preventing direct contact. This liner is designed to contain the feet and can be removed for external cleaning and sterilization. A mechanical interlock prevents the lamp(s) from being activated without the liner in place. The front portion of the device where the tanning lamp and the control devices are located is generally shaped convex, reminiscent of a half sphere. An alternative embodiment of the present invention is envisioned, in which the front portion of the tanning lamp and control device assembly is hinged at on top, thereby allowing it to be opened upward to a predetermined height such that the assembly is fixable in between by means therefore. This allows the lamp to be pointed outward and toward the front of the device, thereby allowing tanning on other parts of the body of a user positioned in the front of the device.

A primary object of the present invention is to provide tanning device for feet.

Another object of the present invention is to provide compact and portable feet tanning device.

Yet another object of the present invention is to eliminate undesirable tan lines by providing gradual tanning exposure.

Still yet another object of the present invention is to incorporate reflective inner surfaces for even tanning.

Another object of the present invention is to provide efficient and energy saving tanning by maximizing reflective inner surface as well as minimizing the distance between the feet and the lamp.

Yet another object of the present invention is to provide for the cleaning and sterilization of areas in contact with the user's skin by means of a removable, light transmitting feet compartment.

Yet another object of the present invention is to provide easily accessible control knobs on the front of the device for timing and power engagement.

Another object of the invention is to provide transparent safety lining for the feet from the hot lamp surface and from the heat of the lamp.

Yet another object of the invention is to provide cooling fan to regulate the temperature inside the device.

Yet another object of the invention is to provide pivoting mechanism on the lamp assembly so that they can be swung open facing outside, thereby making it possible for the device to be used for tanning other parts of the body that could not be put inside of the tanning device.

Still yet another object of the present invention is to manufacture the feet-tanning device economically, thereby making the device available at home, which eliminates the need to make trips to tanning spa or the use of tanning cream.

Additional objects of the present invention will appear as the description proceeds.

The present invention overcomes the shortcomings of the prior art by providing a compact, energy efficient, multi-functional tanning device with a lamp that can be energized to emit UVA and/or UVB rays. In an additional element a panel can be pivoted to tan other body parts.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
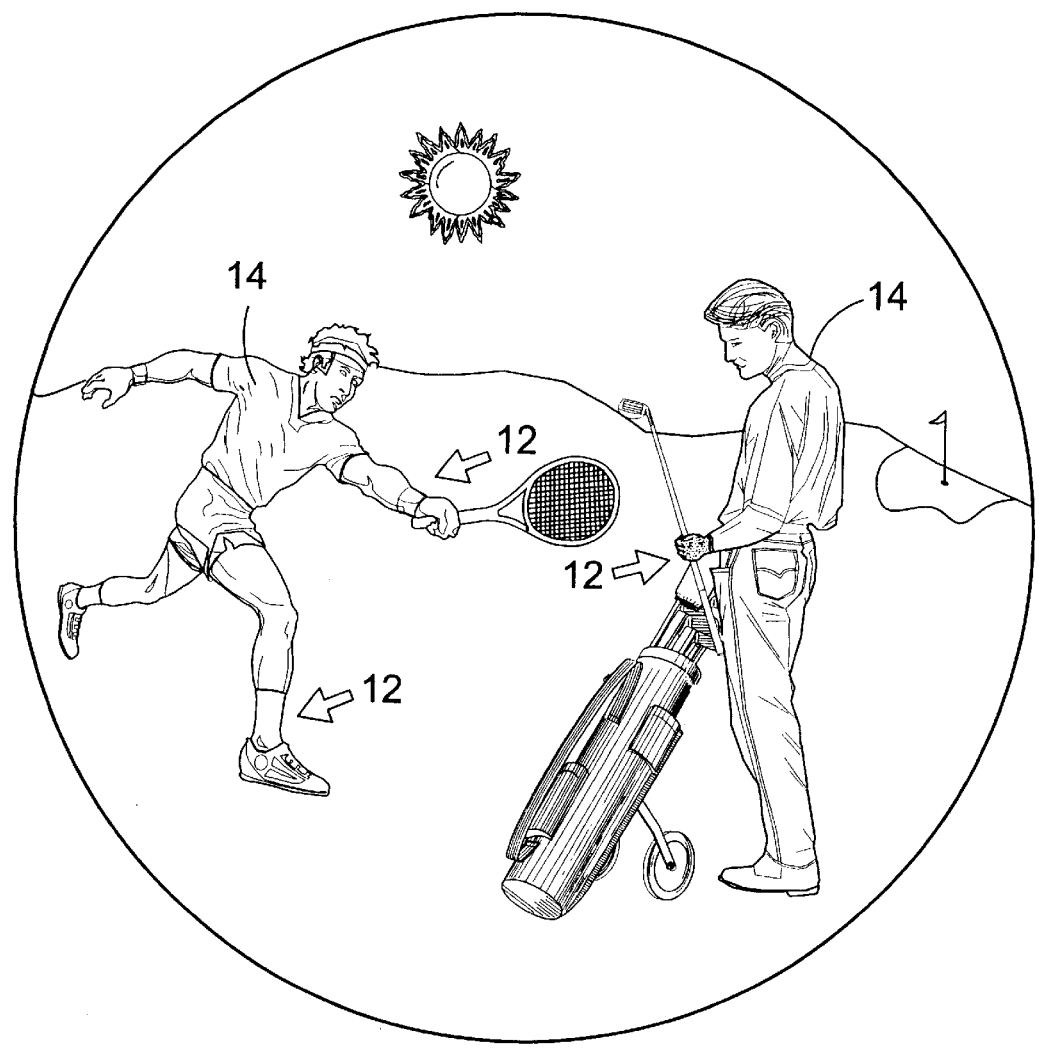
FIG. 1 is a perspective view of leisure activities leading to undesirable tan lines.

With regard to reference numerals used, the following numbering is used throughout the drawings.

10 present invention
12 tan line
14 person
15 base of tanning lamp
16 tanning lamp
17 beams/rays
18 foot
19 hand 20 removable compartment
22 interlock switch
24 power cord
26 fan
27 fan inlet
28 reflective surface
30 enclosure
32 access opening
34 timer
36 cavity
38 hinge
40 hinged cover
42 handle
44 support arm
46 reflector element
48 attachment means

DETAILED DESCRIPTION OF THE PREFERRED EMBODIMENT

The following discussion describes in detail one embodiment of the invention. This discussion should not be construed, however, as limiting the invention to those particular embodiments, practitioners skilled in the art will recognize numerous other embodiments as well. For a definition of the complete scope of the invention, the reader is directed to the appended claims.

Turning to FIG. 1, shown therein is a perspective view of leisure activities leading to undesirable tan lines 12 on a person 14. Outdoor activities often lead to tan lines 12 of undesirable locations such as the hand, foot, and other areas unexposed to the sun. Such tan lines 12 can be unsightly and embarrassing. To develop a uniform tan line can be troublesome or untimely.

Figure 2:
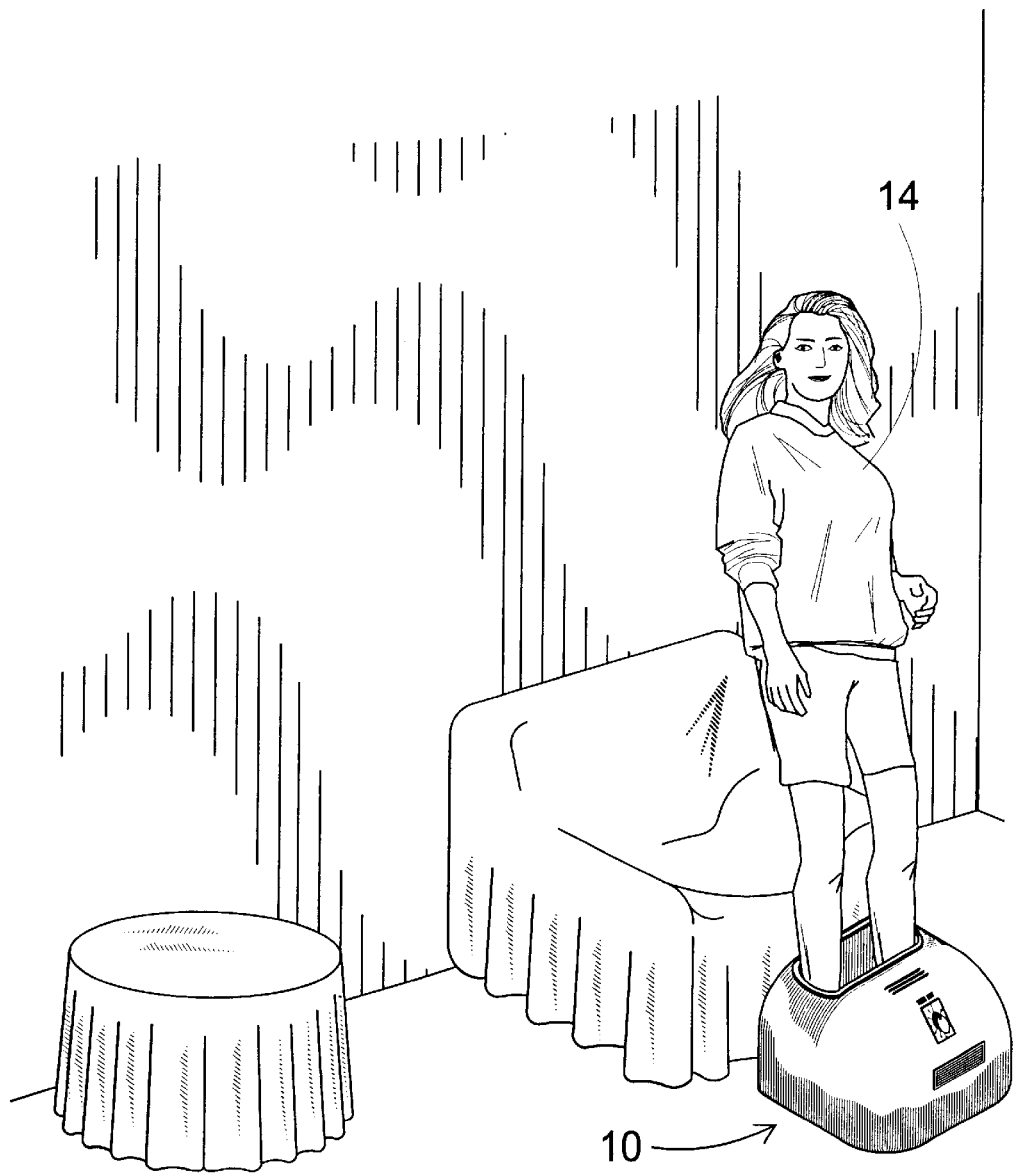
FIG. 2 is a perspective view of the present invention, the portable tanning device, in use.

Turning to FIG. 2, shown therein is a perspective view of the present invention 10, a portable tanning device in use. A woman user 14 using the present invention 10 is able to rid herself of a tan line produced by wearing socks and shoes. The size and portability of the present invention 10 makes developing a uniform tan easy and convenient.

Figure 3:
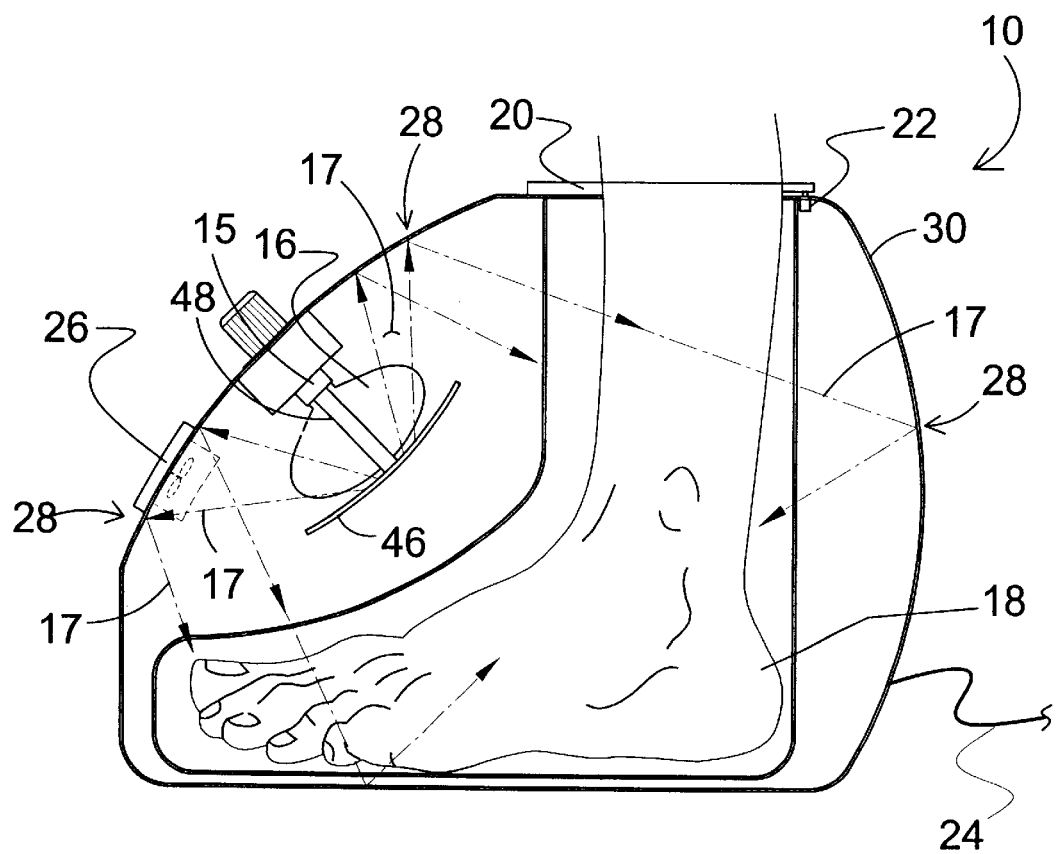
FIG. 3 is a side sectional view of the present invention, the portable tanning device in use.

Turning to FIG. 3, shown therein is a side sectional view of the present invention 10, a portable tanning device in use. The beams or light rays 17 from the tanning lamp light 16 are reflected by a first reflector 46, having attachment means 48 to the tanning lamp base 15, and, then by the reflective surface 28 on the concave inside of enclosure 30 to expose all the skin evenly. The foot 18 is protected from the lamp 16 by a removable clear plastic compartment 20 which is shaped somewhat like a boot in which the foot is inserted. A mechanical interlock switch 22 is used to ensure the compartment is properly placed prior to use. Power cord 24 and fan 26 are also shown.

Figure 4:
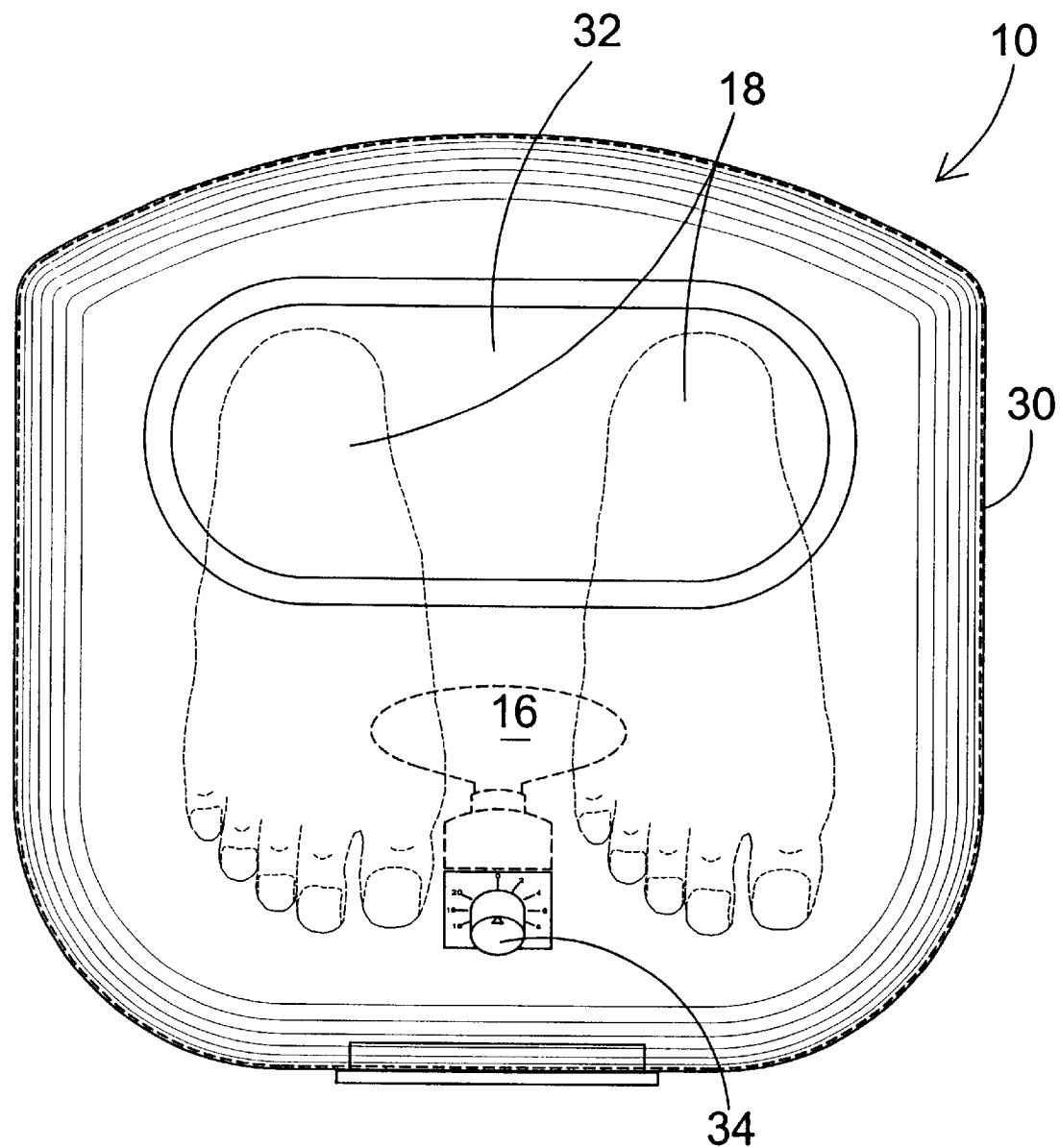
FIG. 4 is a top view of the present invention, the portable tanning device.

Turning to FIG. 4, shown therein is a top view of the present invention 10, a portable tanning device in use. The enclosure tanning device provides adequate space to allow the user to position the feet 18 to allow exposure to all sides of the foot. The removable feet compartment and access opening 32 allow for easy accessibility for cleaning the tanning device after usage and/or servicing the tanning lamp(s) 16. The enclosure 30 and timer 34 are also shown.

Figure 5:
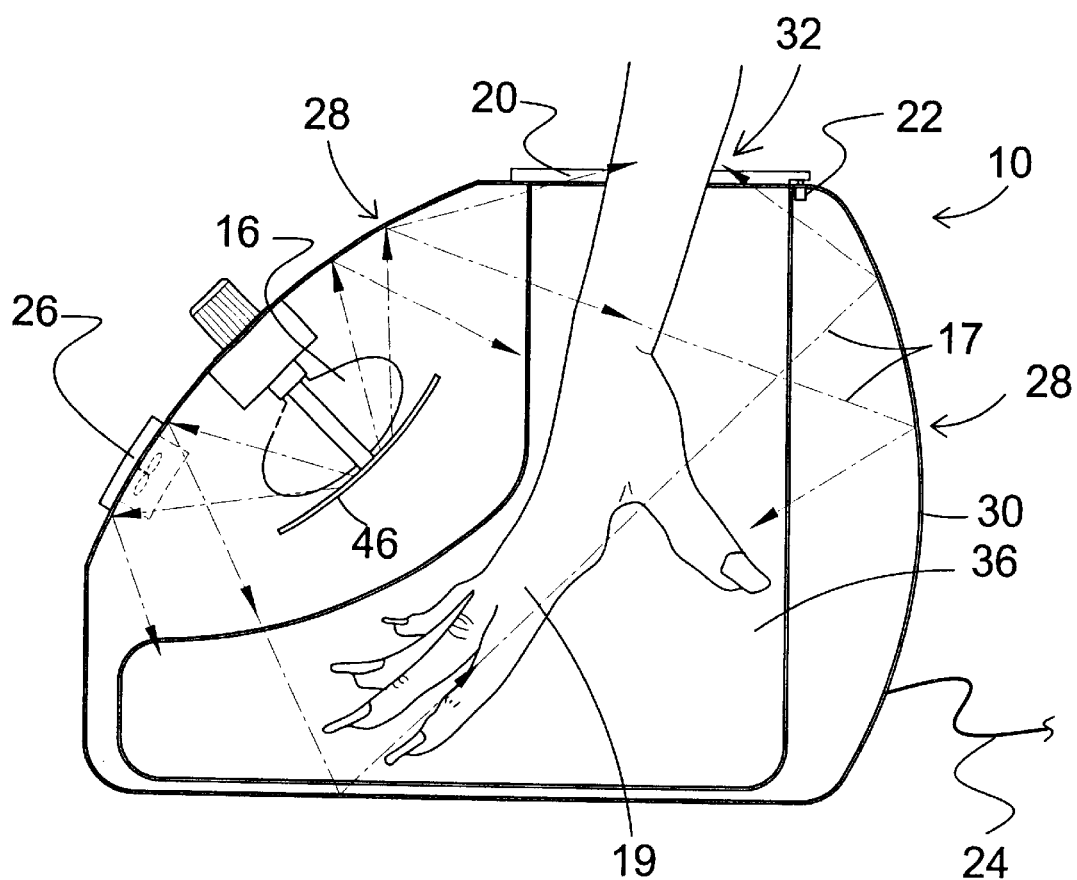
FIG. 5 is a side sectional view of the present invention, the portable tanning device in use.

Turning to FIG. 5, shown therein is a side sectional view of the present invention 10, a portable tanning device in use having a hand 19 inserted therein. The present invention 10 top side opening 32 allows easy insertion into the enclosure 30. The open cavity 36 and reflective surfaces 28 shown by beam direction lines 17 within the enclosure 30 provide for a gradient tanning exposure above the enclosure. Also shown are lamp 16, reflector 46, fan 26, removable compartment 20, interlock switch 22, and power cord 24.

Figure 6:
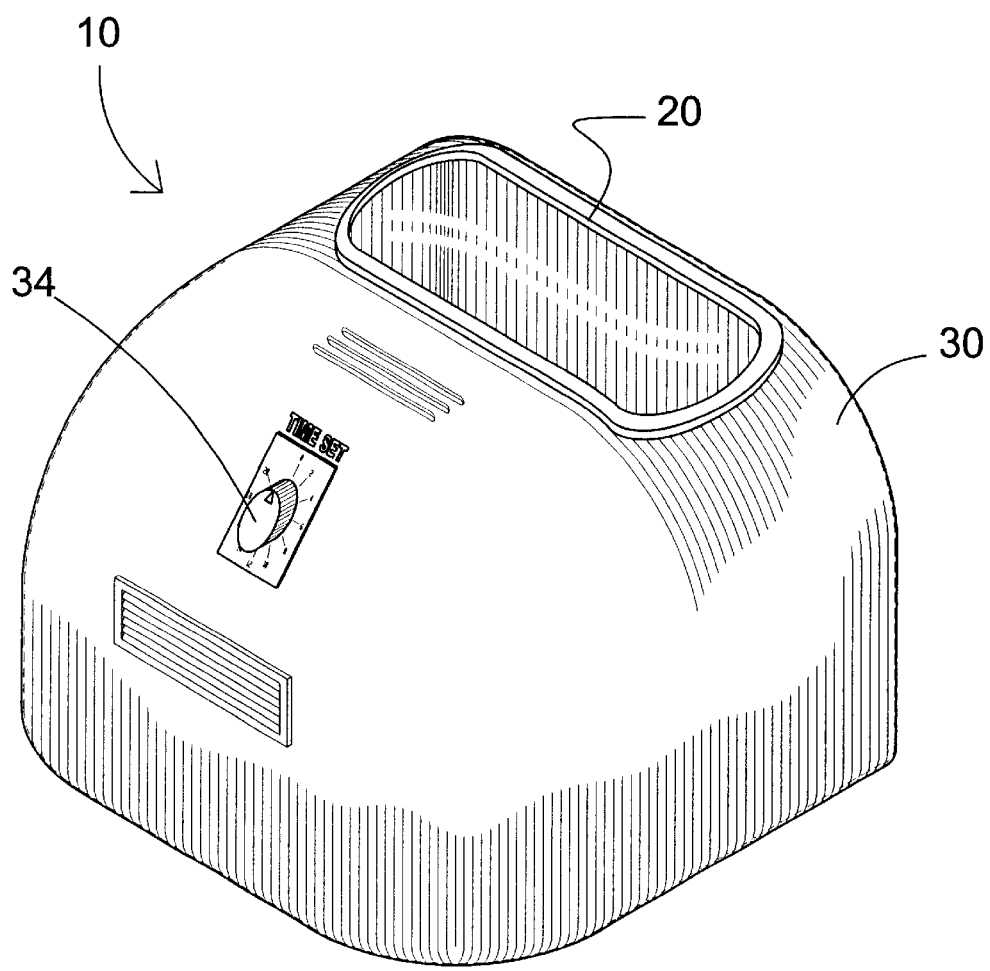
FIG. 6 is an isometric view of the present invention, the portable tanning device.

Turning to FIG. 6, shown therein is an isometric view of the present invention 10, a portable tanning device. The enclosure 30 includes a removable clear plastic liner 20 that forms a separate compartment for the feet and protects the feet from the lamp(s). In addition, the liner 20 is removable for external cleaning and sterilization. The tanning lamp control timer switch 34 attached to the cover 30 is easily accessible while the tanning device is in use. Fan inlet 27 is also shown.

Figure 7:
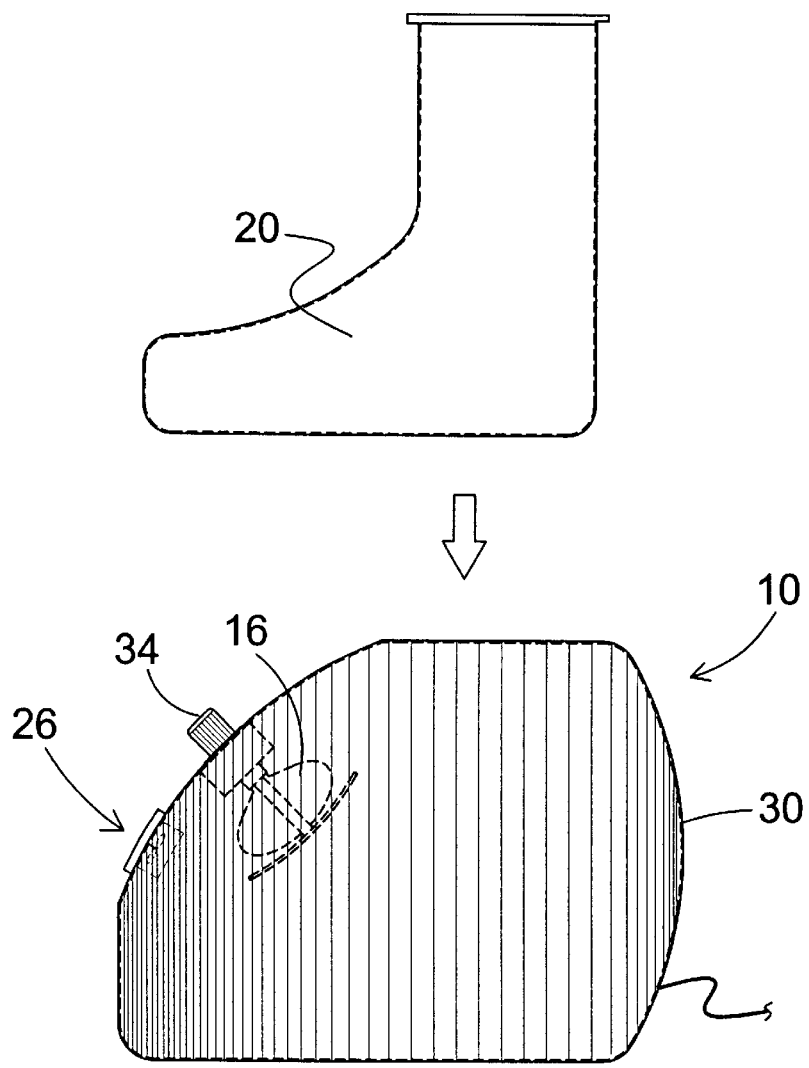
FIG. 7 is a side view of the present invention, the portable tanning device with feet compartment removed.

Turning to FIG. 7, shown therein is a side view of the present invention 10, a portable tanning device with transparent feet compartment 20 removed. The present invention 10 is an enclosure 30 with an electrical powered tanning lamp 16 that enables a person to tan a portion of the body. The lamp 16 is isolated within the enclosure to prevent the skin from contacting the lamp. The interior of the enclosure is composed of a reflective material and is concave to promote a maximum reflection of the light and even coloring or tanning. Also shown are timer switch 34 and fan 26.

Figure 8:
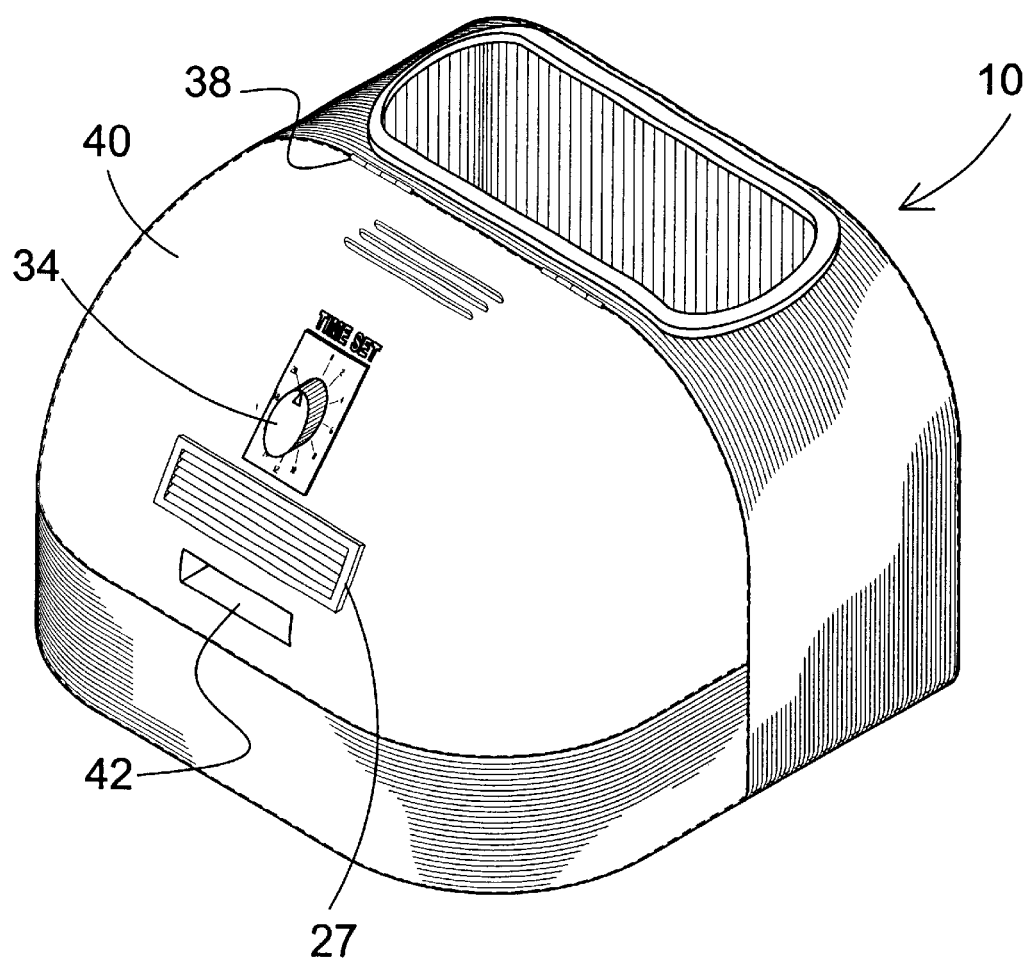
FIG. 8 is an isometric view of the present invention with embodiment, the portable tanning device with hinged cover.

Turning to FIG. 8, shown therein is an isometric view of the present invention 10 with an alternative embodiment, a portable tanning device with a hinged cover 40 with multiple hinges 38. The tanning lamp cover 40 includes a molded handle 42 within to allow the cover to be lifted and gain access to the lamp and provide exterior tanning exposure. The tanning lamp control timer switch 34 attached to the cover is easily accessible while the tanning device 10 is in use. Also shown is inlet 27 of the fan.

Figure 9:
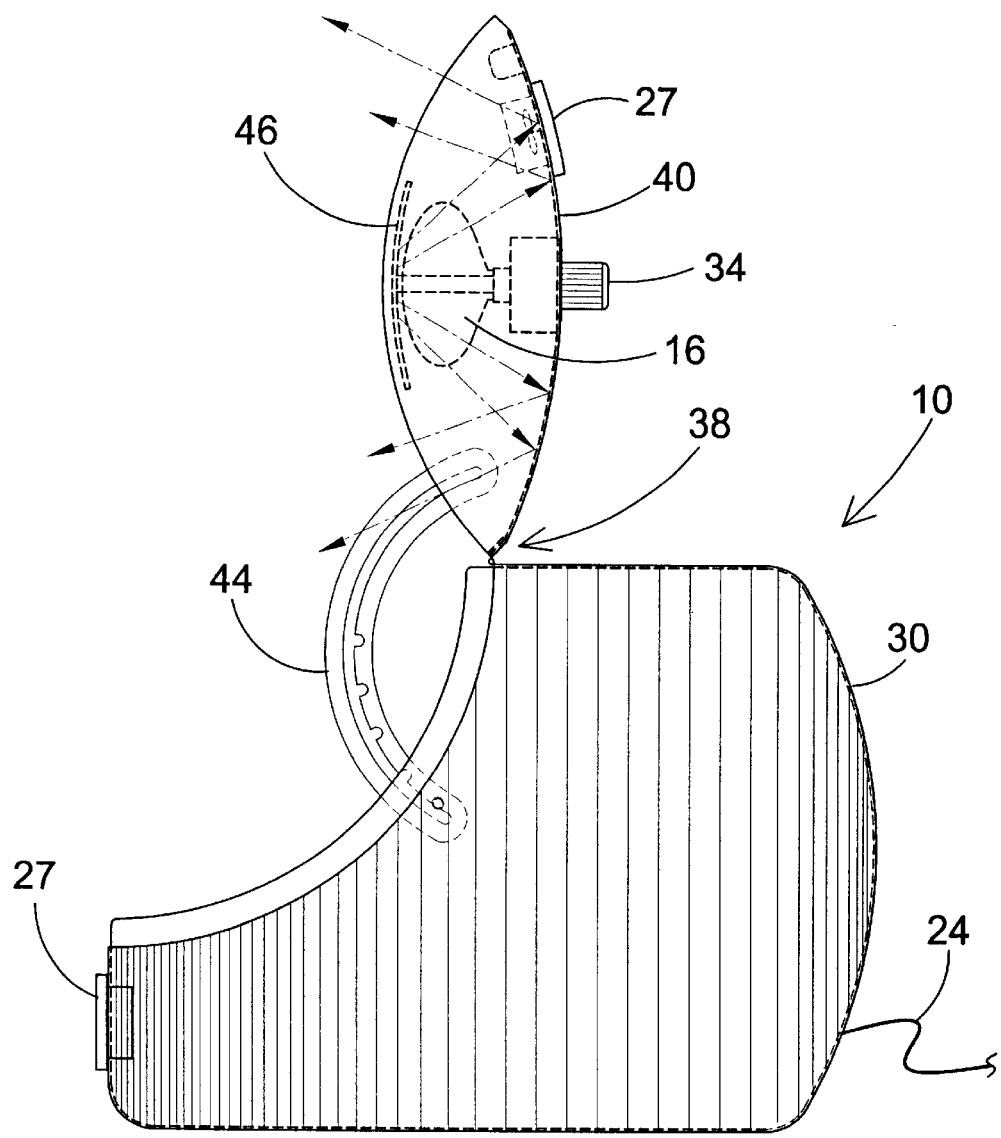
FIG. 9 is a side view of an embodiment of the present invention, the portable tanning device with cover in a retracted position.

Turning to FIG. 9, shown therein is a side view of an embodiment of the present invention 10, a portable tanning device with the cover 40 in a retracted open position. The tanning lamp cover 40 is hinged at 38 on the top side to allow the cover to be rotated about 270 degrees upwardly which provides for tanning a portion of the body outside the enclosure 30. The cover 40 is locked by brace or locking support arm 44 into a desired angled position that directs the tanning lamp toward the desired area of the body. The cover 40 is concave to maximize the area of exposure. Other elements previously disclosed are also shown.

Figure 10:
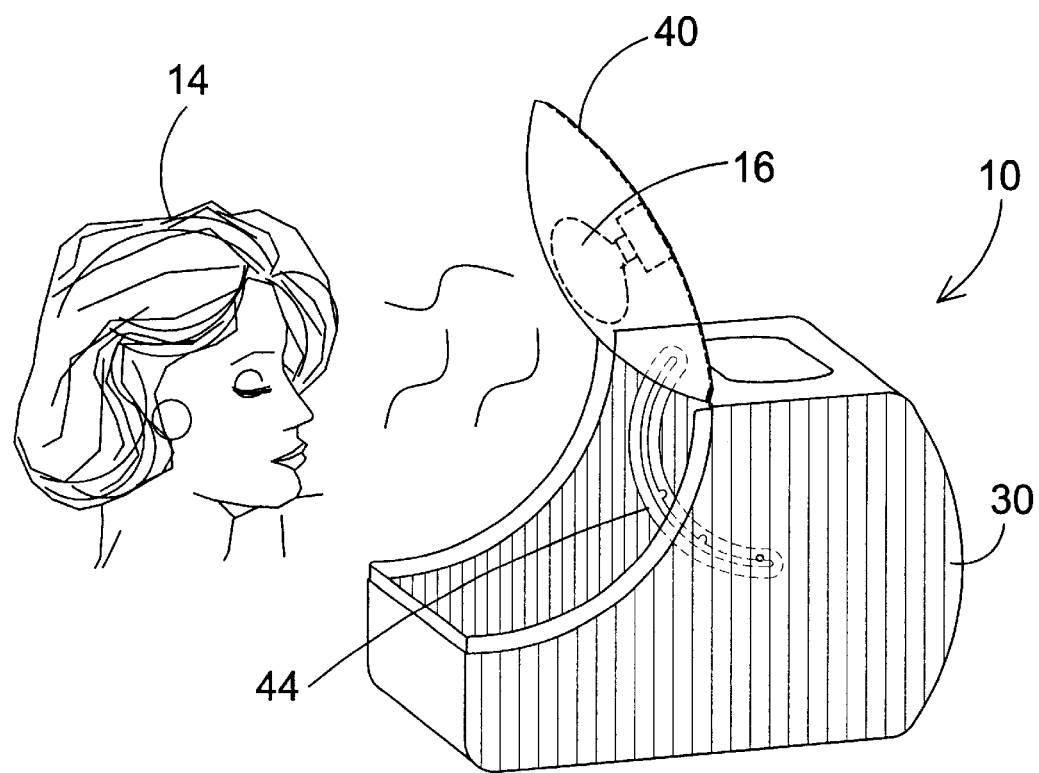
FIG. 10 is a perspective view of the present invention, the portable tanning device, in use.

Turning to FIG. 10, shown therein is a perspective view of the present invention 10, a portable tanning device in use. The portable tanning device 10 allows the user 14 the convenience and comfort of tanning in a domestic setting. In addition, the present invention 10 eliminates the required isolation of typical tanning beds and booths. Other elements previously disclosed are also shown.

We claim:

1. An apparatus for tanning the feet and other body parts of a user, comprising:
   a) an enclosure, said enclosure having a sloping front, a back, a pair of sides, a top, a bottom, and an inner surface and an outer surface, said enclosure having a cavity therein, said cavity having a central area for receiving the feet or other body parts of the user;
   b) wherein said top of said enclosure has an opening therein, said opening for receiving a removable compartment or the feet or other body parts of the user;
   c) wherein said inner surface of said enclosure is reflective to reflect light rays;
   d) wherein said inner surface is concave in shape to reflect light rays about said cavity;
   e) a tanning light disposed on said inner surface of said sloping front of said enclosure to permit light rays to be emitted toward the central area of said cavity, f) a reflector disposed on said tanning light between said tanning light and said central area of said cavity to permit light rays to be scattered and directed toward a plurality of points on the inner reflective surface of the enclosure; and, g) means for controlling said tanning light whereby the operation of the tanning light is controlled.

2. The apparatus of claim 1, further comprising a removable compartment for receiving the feet or other body parts of the user being disposed internal said enclosure.

3. The apparatus of claim 2, wherein said removable compartment is made of transparent plastic so that the feet or other body parts of the user are not burned.

4. The apparatus of claim 3, wherein said removable compartment is boot-shaped to receive the feet or other body parts of a user.

5. The apparatus of claim 4, further comprising an interlock switch disposed on said removable compartment to prevent operation of the apparatus without the removable compartment.

6. The apparatus of claim 5, wherein said means for controlling said tanning light comprises:

a) a power supply to permit operation of the tanning light; and, b) a timer to permit the timed operation of the tanning light.

7. The apparatus of claim 6, further comprising a fan disposed on said enclosure to permit outside air to be transferred into the enclosure to remove the heat produced by the tanning lamp.

8. An apparatus for tanning the feet and other body parts of a user, comprising:

a) an enclosure, said enclosure having a sloping front, a back, a pair of sides, a top, a bottom, and an inner surface and an outer surface, said enclosure having a cavity therein, said cavity having a central area for receiving the feet or other body parts of the user;

b) wherein said top of said enclosure has an opening therein, said opening for receiving a removable compartment or the feet or other body parts of the user;

c) wherein said inner surface of said enclosure is reflective to reflect light rays;

d) wherein said inner surface is concave in shape to reflect light rays about said cavity;

e) a tanning light disposed on said inner surface of said sloping front of said enclosure to permit light rays to be emitted toward the central area of said cavity;

f) a reflector disposed on said tanning light between said tanning light and said central area of said cavity to permit light rays to be scattered and directed toward a plurality of points on the inner reflective surface of the enclosure;

g) means for controlling said tanning light whereby the operation of the tanning light is controlled;

h) a cover substantially forming said sloping front of said enclosure, said cover having a top edge, a bottom edge, and a pair of sides; and, i) at least one hinge for attaching said cover to said enclosure to permit the cover to rotate upwardly about 270 degrees away from the central area of the enclosure to permit the tanning light to point toward the front outside of the enclosure.

9. The apparatus of claim 8, further comprising a removable compartment for receiving the feet or other body parts of the user being disposed internal said enclosure.

10. The apparatus of claim 9, wherein said removable compartment is made of transparent plastic so that the feet or other body parts of the user are not burned.

11. The apparatus of claim 10, wherein said removable compartment is boot-shaped to receive the feet or other body parts of a user.

12. The apparatus of claim 11, further comprising an interlock switch disposed on said removable compartment to prevent operation of the apparatus without the removable compartment.

13. The apparatus of claim 12, wherein said means for controlling said tanning light comprises:

a) a power supply to permit operation of the tanning light; and, b) a timer to permit the timed operation of the tanning light.

14. The apparatus of claim 13, further comprising a fan disposed on said enclosure to permit outside air to be transferred into the enclosure to remove the heat produced by the tanning lamp(s).

15. The apparatus of claim 13, further comprising means for locking the cover in an upward position, whereby the cover may be secured in the upward position.

16. The apparatus of claim 15, further comprising a handle disposed on said cover to permit the cover to be easily opened.

* * * * *